US00PP32501P2

(12) United States Plant Patent
Travers

(10) Patent No.: US PP32,501 P2
(45) Date of Patent: Nov. 24, 2020

(54) ***TRACHELOSPERMUM* PLANT NAMED 'TRARED'**

(50) Latin Name: *Trachelospermum jasminoides*
Varietal Denomination: TRARED

(71) Applicant: Arnaud Travers, St Jean le Blanc (FR)

(72) Inventor: Arnaud Travers, St Jean le Blanc (FR)

( * ) Notice: Subject to any disclaimer, the term of this patent is extended or adjusted under 35 U.S.C. 154(b) by 0 days.

(21) Appl. No.: 16/602,463

(22) Filed: Oct. 10, 2019

(51) Int. Cl.
*A01H 5/02* (2018.01)
*A01H 6/08* (2018.01)

(52) U.S. Cl.
USPC ..... Plt./226
CPC ..... *A01H 6/08* (2018.05)

(58) Field of Classification Search
USPC ..... Plt./226
CPC ..... A01H 6/08; A01H 5/02
See application file for complete search history.

*Primary Examiner* — Keith O. Robinson
(74) *Attorney, Agent, or Firm* — Cassandra Bright

(57) ABSTRACT

A new and distinct *Trachelospermum* hybrid named 'TRARED' is disclosed, characterized by distinctive red Fall and Winter foliage, and a dense plant form. Plants flower abundantly and produce elliptic, glossy foliage. The new cultivar is a *Trachelospermum* typically suited for ornamental container and landscape use.

5 Drawing Sheets

Latin name of the genus and species: *Trachelospermum jasminoides*.
Variety denomination: 'TRARED'.

BACKGROUND OF THE INVENTION

The new cultivar is the result of chance discovery in France. The new variety was discovered as a naturally occurring whole plant mutation of an unnamed, unpatented *Trachelospermum jasminoides*. The new variety was discovered in February of 2011 at a commercial nursery in Saint Cyr en Val, France.

After selecting and isolating the new cultivar, asexual reproduction of the new cultivar 'TRARED' was first performed in Saint Cyr en Val, France, by terminal vegetative cuttings in July 2011. The inventor isolated the interesting new plant and continued confidential testing for stability over time. Since July of 2011 'TRARED' has since produced multiple generations, and has shown that the unique features of this cultivar are stable and reproduced true to type.

SUMMARY OF THE INVENTION

The cultivar 'TRARED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRARED'. These characteristics in combination distinguish 'TRARED' as a new and distinct *Trachelospermum* cultivar:

1. Unique red foliage color beginning in Fall and continuing through Winter
2. Abundant flowering.
3. Narrower foliage.
4. Glossy foliage.
5. Smaller mature plant size.

PARENTAL COMPARISON

The new variety is similar to the parent in most horticultural characteristics, however plants of the new variety differ in the following:

1. Foliage color of the new variety is red in the Winter and Spring, whereas the parent variety has green and brown Winter foliage.
2. Plants of the new variety are observed evergreen, plants of the parent variety are somewhat deciduous comparatively.
3. Plants of the new variety flower more abundantly than plants of the parent variety.
4. Foliage of the new variety is narrower and glossier than foliage of the parent variety.
5. Mature plant size of the new variety is smaller than mature plants of the parent variety.

COMMERCIAL COMPARISON

Plants of the new cultivar 'TRARED' are similar to the commercial variety *Trachelospermum* 'Rose' unpatented, in most horticultural characteristics. However, the new variety differs from 'Rose' in the following:

1. Foliage color of the new variety is red in the Winter and Spring, whereas this comparator has green Winter Foliage.
2. Flowers of the new variety are white, flowers of this comparator are pink.
3. Plants of the new variety flower more abundantly than plants of 'Rose'.
4. Foliage of the new variety is narrower and glossier than foliage of 'Rose'.
5. Mature plant size of the new variety is smaller than mature plants of 'Rose'.

BRIEF DESCRIPTION OF THE PHOTOGRAPHS

The accompanying photograph in FIG. 1 illustrates in full color a typical plant of 'TRARED' grown outdoors in France at approximately 8 months of age.

Figure 1:
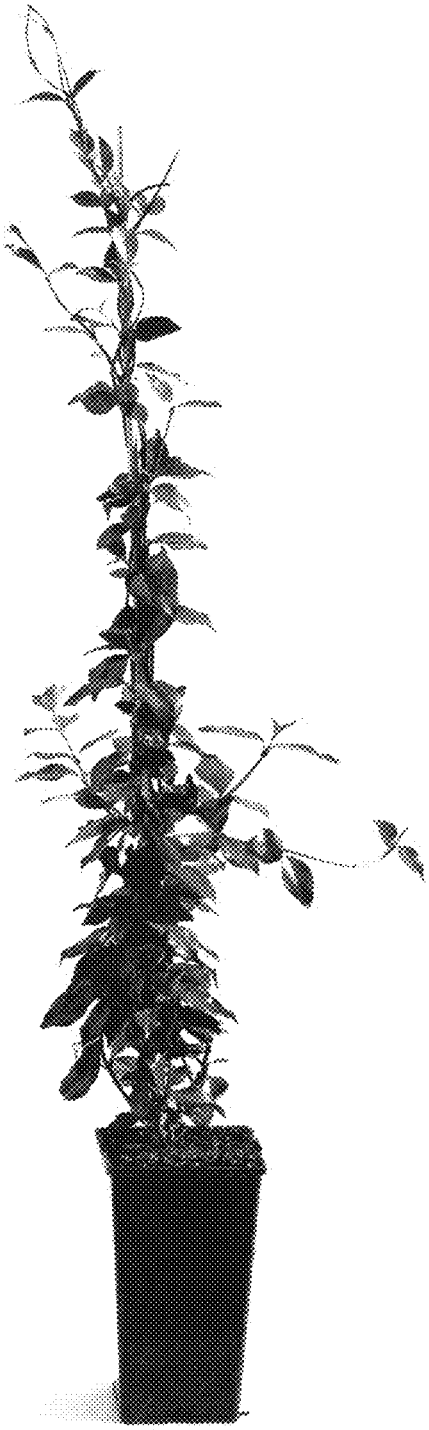
Figure 2:
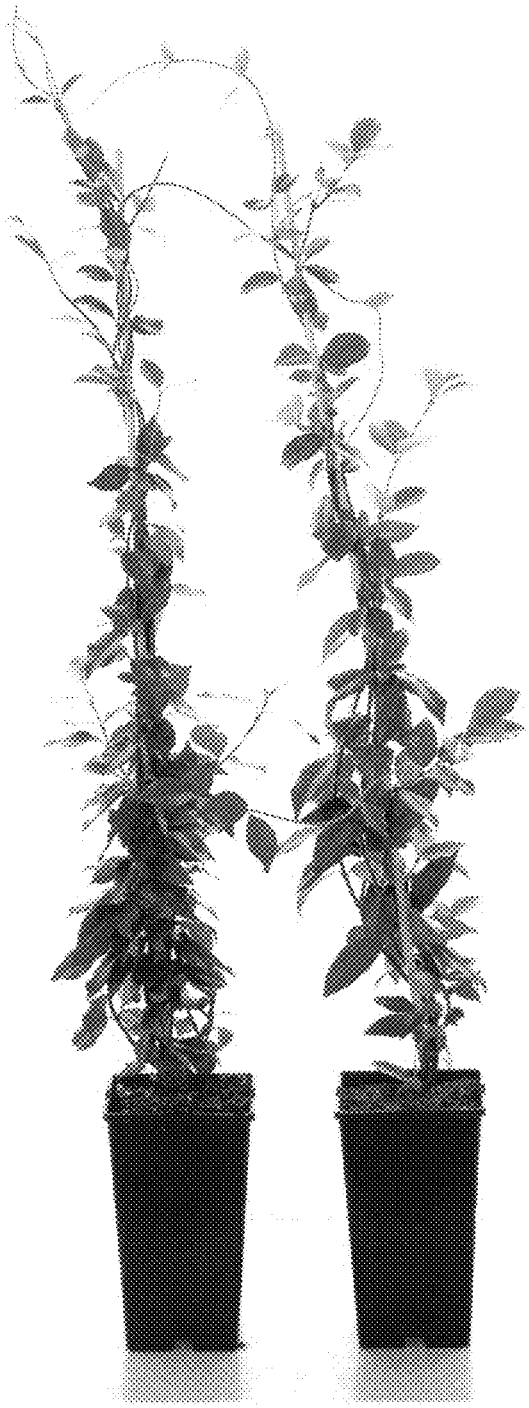
FIG. 2 is a comparison photograph of the new variety and the parent variety. 'TRARED' is on the left of the photograph, the parent variety is on the right.
Figure 3:
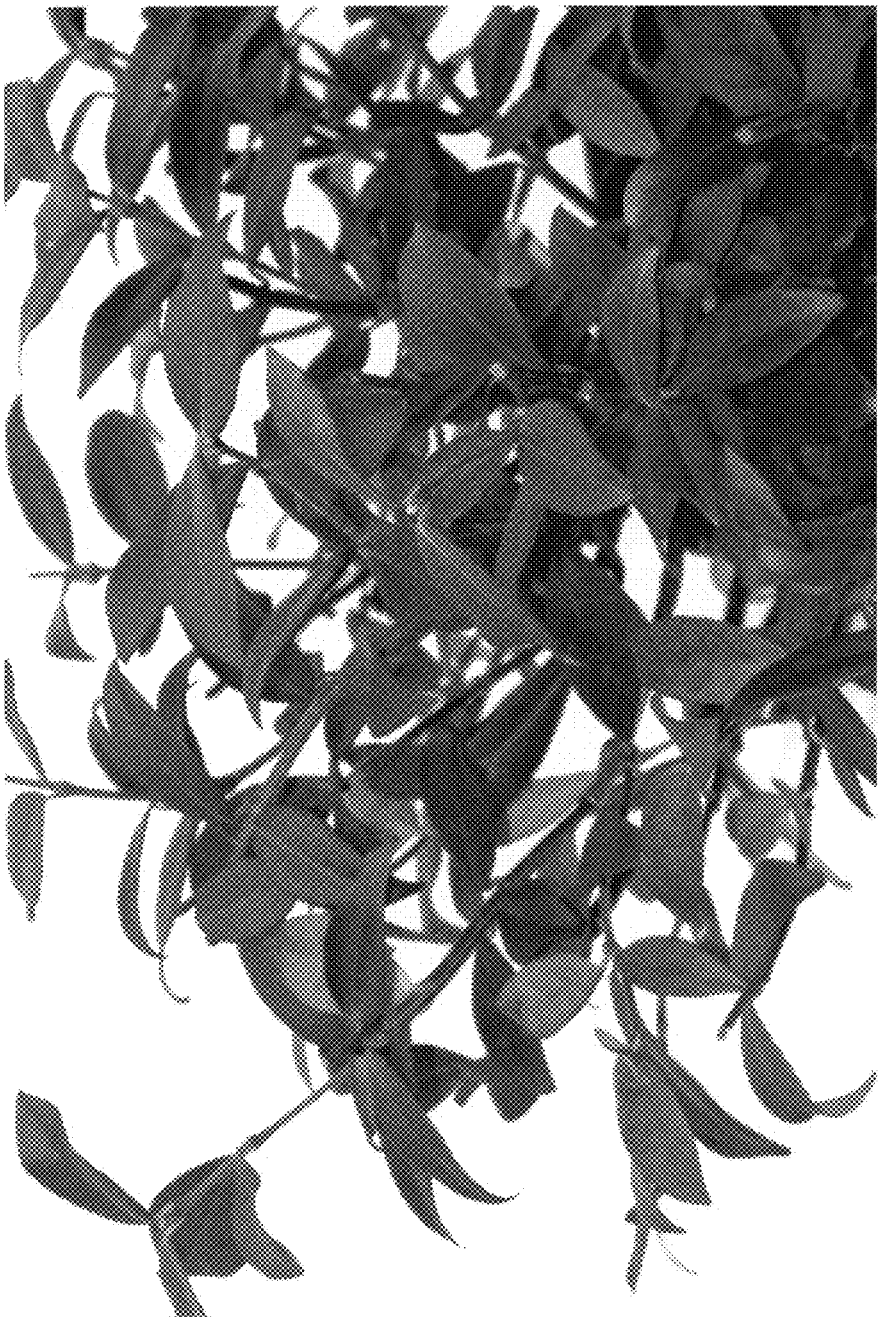
FIG. 3 illustrates Fall foliage color of 'TRARED'.
Figure 4:
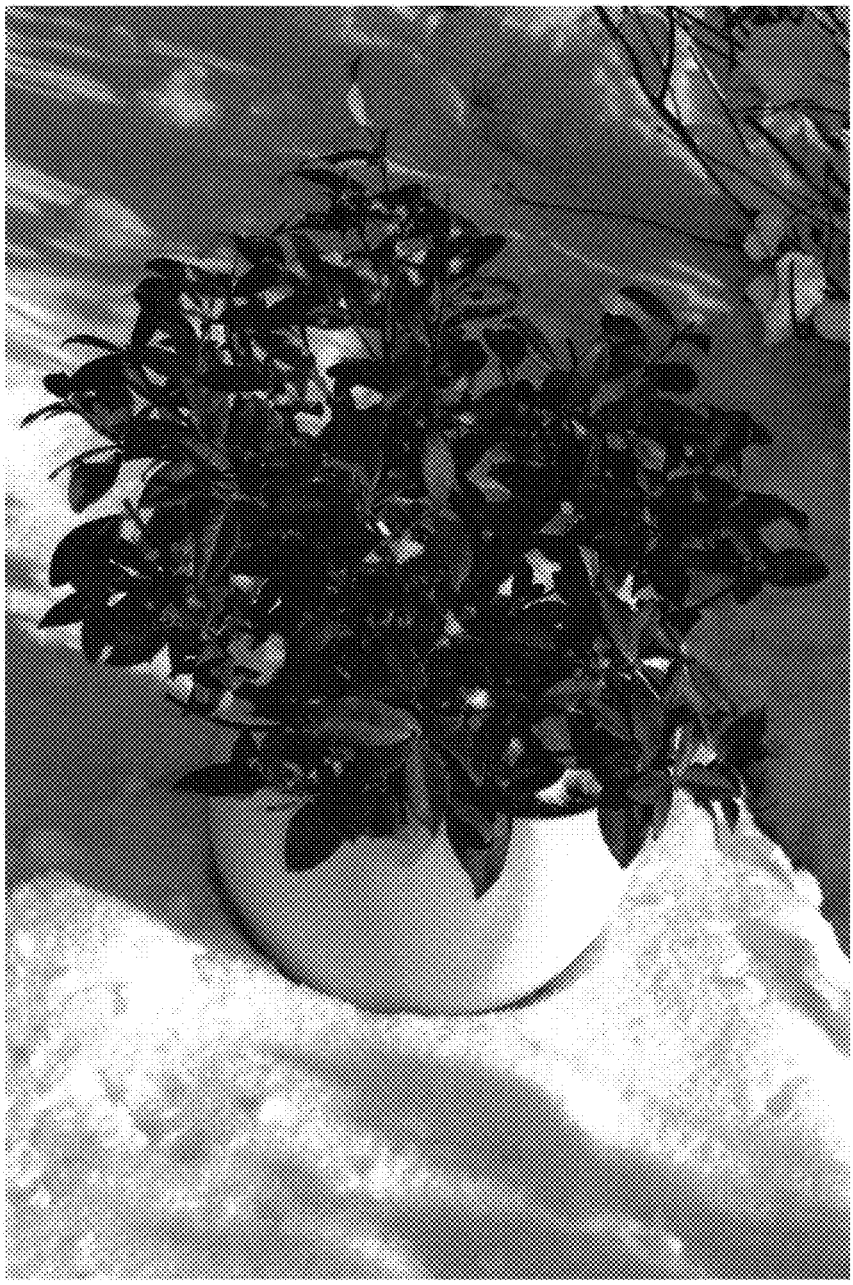
FIG. 4 shows Winter foliage color.
Figure 5:
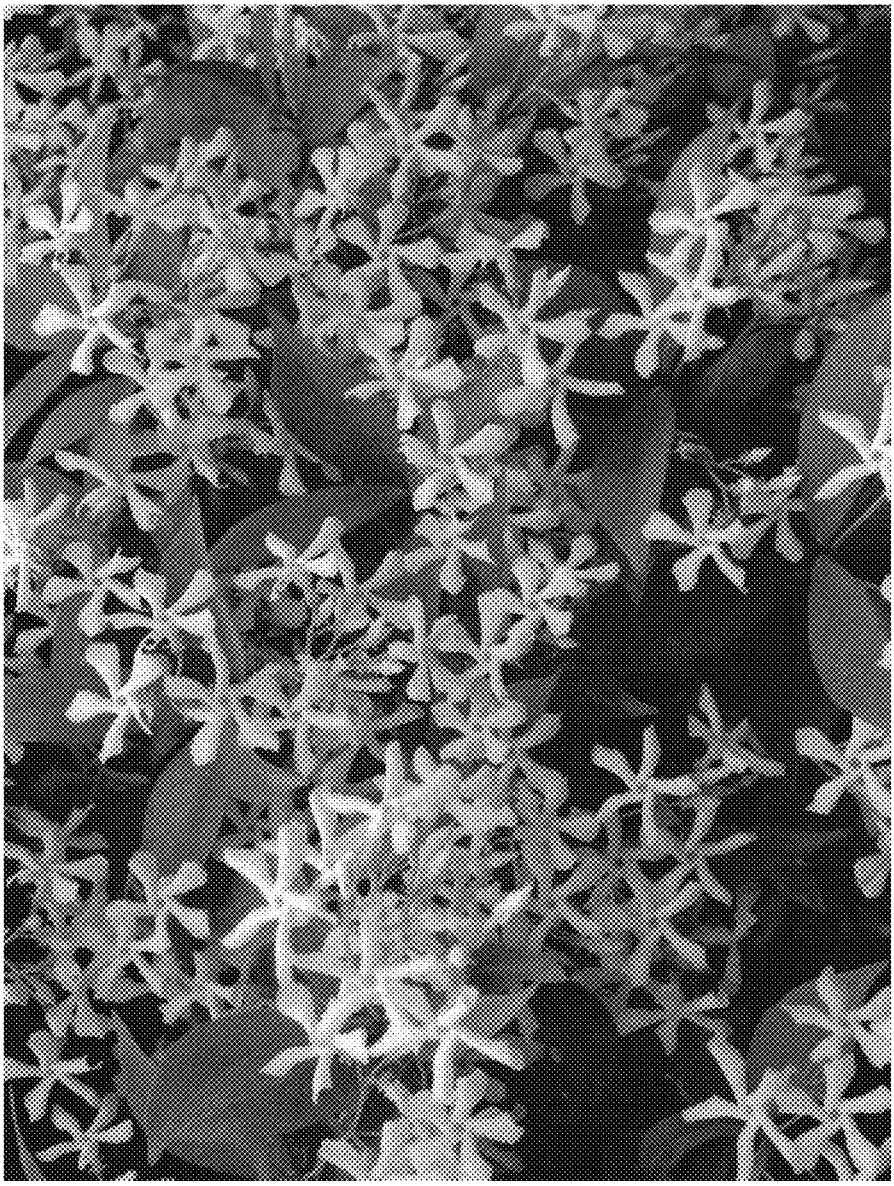
FIG. 5 illustrates flowers and foliage in late Spring.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TRARED' plants grown outdoors in France. The growing temperature ranged from 0° C. to 25° C. at night to 0° C. to 30° C. during the day. No artificial light, photoperiodic treatments or chemical treatments were given to the plants. Plants were pinched once. Measurements and numerical values represent averages of typical flowering types.

Botanical classification: *Trachelospermum jasminoides* 'TRARED'.

Age of the plant described: Approximately 18 months.

Container size of the plant described: 2 gallon.

PROPAGATION

Typical method: Vegetative cuttings.

Time to initiate root developments: 21 days in the summer at 22° to 25° C.

Time to produce a rooted cutting/young plant: 40-50 days in the summer at 20° to 26° C.

Root description: Fine, fibrous. Brown, not accurately measured with a color chart.

PLANT

Growth habit: Shrubby climbing vine. Evergreen, foliage replaced non-seasonally.

Height: Variable, approximately 200 to 300 cm at maturity. Plant spread: Variable, approximately 30 cm, trained up a single trellis pole.

Branching characteristics: One main stem, easily making side branches from a pinch.

Length of main stem: Approximately 190 to 280 cm at maturity.

Diameter of main stem: Approximately 0.2 cm.

Main stem color: Near RHS Green 137C, heavily flushed Greyed-Red 178B.

Main stem texture: Glabrous.

Internode length: Average range about 1.0 to 1.9 cm.

Strength: Strong, flexible, semi-woody.

FOLIAGE

Leaf:

*Arrangement*.—Alternate or sub-opposite, single.

*Average length*.—Approximately 5.5 to 6.5 cm.

*Average width*.—Approximately 2 cm.

*Shape of blade*.—Elliptical.

*Apex*.—Acute.

*Base*.—Attenuate.

*Attachment*.—Stalked.

*Margin*.—Entire.

*Texture of both surfaces*.—Glabrous.

*Attitude*.—Horizontal.

*Quantity*.—Average 8 to 12 per lateral stem.

*Fragrance*.—None detected.

*Color*.—Young foliage upper side: Near RHS Green 143C. Young foliage under side: Near RHS Yellow-Green 143C. Mature foliage upper side: Near RHS Green 137A. Mature foliage under side: Near RHS Green 137C. Fall foliage upper side: Near RHS Greyed-Red 181A. Fall foliage under side: Near RHS Greyed-Red 178B. Winter foliage upper side: Near RHS Greyed-Purple 183B. Winter foliage under side: Near RHS Greyed-Purple 183C.

*Venation*.—Type: Pinnate. Color: Upper surface: Near RHS Yellow-Green 144C. Lower surface: Near RHS Yellow-Green 144C.

Petiole:

*Length*.—Approximately 0.3 cm.

*Diameter*.—Approximately 0.2 cm.

*Texture*.—Smooth.

*Color*.—Near RHS Yellow-Green 144C.

Stipules: Not observed.

FLOWER

Bloom period:

*Natural season*.—Late Spring to mid-summer.

*Flower type and habit*.—Axillary, solitary, rotate. Flowers facing upward. Individual flowers last about 2 to 5 days, depending upon environmental conditions. A mature plant has about 3000 to 4000 open flowers at one time.

Petals:

*Arrangement*.—Non-overlapping single whorl.

*Quantity*.—Typically 5 per flower.

*Size*.—Length: Approximately 2.5 to 3.0 cm. Depth: Approximately 1.0 to 1.5 cm.

*Margin*.—Entire slightly curved downward.

*Apex*.—Acute.

*Base*.—Fused.

*Texture*.—Smooth all surfaces.

*Shape*.—Spatulate.

Color:

*Petals*.—When opening: Upper surface: Near RHS White 155C. Lower surface: Near RHS White 155C. Fully opened: Upper surface: Near RHS White 155C. Lower surface: Near RHS White 155C. Ageing: Upper surface: Near RHS White 155C. Lower surface: Near RHS White 155C.

Sepals:

*Arrangement*.—Campanulate, lower half fused, upper portion 5 sepal lobes.

*Quantity*.—Typically 5 per flower.

*Size*.—Width: Approximately 1.0 cm. Depth: Approximately 1.0 cm.

*Shape*.—Unfused portion deltate.

*Margin*.—Entire slightly curved downward.

*Apex*.—Acute.

*Base*.—Fused.

*Texture*.—Smooth.

*Color*.—Near RHS Green 143C.

Bud:

*Shape*.—Conical.

*Length*.—Approximately 1.0 cm.

*Diameter*.—Approximately 0.5 cm.

*Color*.—Near RHS Green-White 157A.

Peduncles:
*Length*.—Average range about 2 to 3 cm.
*Width*.—Approximately 0.2 cm.
*Strength*.—Flexible.
*Color*.—Near RHS Green 143C.
Fragrance: Strong, sweet.

REPRODUCTIVE ORGANS

Stamens:
*Number*.—Average 5.
*Stamen length*.—Approximately 0.9 cm.
*Stamen color*.—Near White N155B.
*Anther length*.—Approximately 0.3 cm.
*Anther color*.—Near RHS Yellow-White 158B.
*Anther shape*.—Narrow deltoid.
*Pollen quantity*.—Scant.
*Pollen color*.—Near White N155C.
Pistil:
*Length*.—Approximately 0.8 cm.
*Style length*.—Approximately 0.6 to 0.8 cm.
*Style color*.—Near White 155A.
*Stigma*.—Shape: Linear. Color: Near RHS White 155A.

OTHER CHARACTERISTICS

Seeds and fruits: Not observed to date.
Disease/pest resistance: Neither resistance nor susceptibility to normal pests of *Trachelospermum* has been observed. Better resistance for mildew diseases of *Trachelospermum* has been observed. The most common known mildew pathogen is *Erysiphe aquilegiae*.
Temperature tolerance: Tolerates temperatures from approximately −15° C. to 38° C.

What is claimed is:

1. A new and distinct cultivar of *Trachelospermum* hybrid plant named 'TRARED' as herein illustrated and described.

* * * * *